United States Patent [19]

Riccardi

[11] 3,941,835

[45] Mar. 2, 1976

[54] RECOVERY OF L-DOPA FROM R-DOPA CONTAINING MATERIALS

[75] Inventor: Guy J. Riccardi, Freeport, N.Y.

[73] Assignee: Bio-Derivatives Corporation, Deer Park, N.Y.

[22] Filed: Mar. 19, 1970

[21] Appl. No.: 21,072

[52] U.S. Cl. ............................................... 260/519
[51] Int. Cl.$^2$ ...................................... C07C 101/77
[58] Field of Search .................................... 260/519

[56] References Cited
UNITED STATES PATENTS 3,253,023   5/1966   Wysong ............................. 260/519

*Primary Examiner*—Richard L. Raymond
*Attorney, Agent, or Firm*—Cooper, Dunham, Clark, Griffin & Moran

[57] ABSTRACT

L-Dopa is recovered from velvet bean and other L-Dopa containing materials by water extraction, preferably carried out at a temperature in the range 15–25°C. The resulting L-Dopa aqueous extract is then concentrated and the resulting concentrated extract treated or cooled to crystallize L-Dopa therefrom.

19 Claims, 1 Drawing Figure

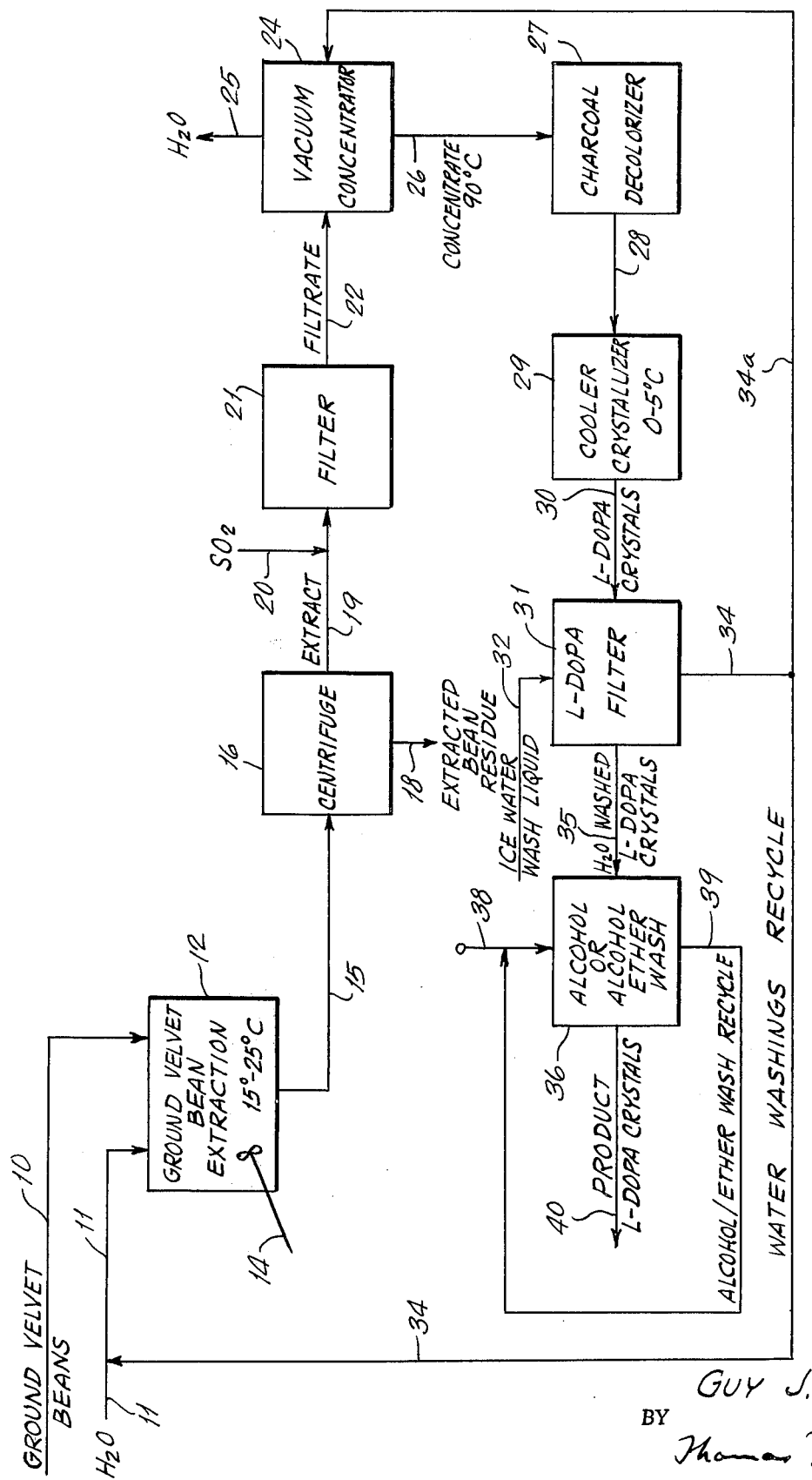

RECOVERY OF L-DOPA FROM R-DOPA CONTAINING MATERIALS

This invention relates to L-Dopa. More particularly, this invention relates to the recovery of L-Dopa from velvet bean, either whole velvet bean including pod or stem or ground velvet bean.

It is known that certain leguminous plants and seeds, such as velvet bean (Vicia Faba) contain L-Dopa and it is known that L-Dopa can be extracted from ground velvet bean by acidified water, see the article by E. R. Miller entitled "Dihydroxyphenylalanine, a Constituent of the Velvet Bean", J. Biol. Chem. 44, 481–486 (1920), the article entitled "B-3,4-Dihydroxyphenyl-L-Alanine" by R. R. Sealock, Biochemical Preparations, Vol. I, page 25 (1949) and Wysong U.S. Pat. No. 3,253,023 (1966). The disclosures of each of the above-identified publications are herein incorporated and made part of this disclosure.

L-Dopa is also extractible from such L-Dopa containing materials as vetch, broad beans, especially Georgia velvet bean, and the African Sommerset bean, as well as the seeds of Mucuna puriens (L) DC Leguminosae.

In the extraction of ground velvet bean by means of acidified water, difficulty has been experienced in separating the aqueous L-Dopa-containing extract by filtration from the extracted ground velvet bean due to the solubilization of the water-soluble constituents. These water-soluble constituents cause difficulties when it is attempted to separate the aqueous extract phase from the extracted ground velvet bean, such as by filtration or centrifugation or settling, or to concentrate the aqueous extract phase.

It is an object of this invention to provide an improved process for the extraction of L-Dopa from L-Dopa-containing materials, such as velvet bean, e.g. whole and ground velvet bean.

It is another object of this invention to provide an improved process for the separation of an aqueous L-Dopa containing extract by filtration from extracted velvet bean.

It is another object of this invention to provide an improved process for the purification of L-Dopa.

How these and other objects of this invention are achieved will become apparent in the light of the accompanying disclosure made with reference to the accompanying drawing which is a flow sheet embodying the practices of this invention directed to the extraction and recovery of L-Dopa from ground velvet bean.

In at least one embodiment of the practice of this invention at least one of the foregoing objects will be achieved.

In accordance with this invention L-Dopa is extracted from L-Dopa-containing materials, such as ground velvet bean, by contacting the material with water, desirably at a temperature in the range from about 15° to about 25°C. Following the extraction operation the resulting L-Dopa-containing aqueous extract is separated from the original L-Dopa-containing material, such as by centrifugation and/or filtration. The resulting aqueous L-Dopa-containing extract or filtrate is then subjected to concentration for the removal of a substantial amount of the water content, at least about 50%, preferably up to about 90%, of the water content by vacuum concentration, i.e. evaporative removal of the water at a reduced pressure, at a pressure below 760 mm Hg. absolute, such as at a pressure in the range 2–500 mm Hg absolute. The concentrated L-Dopa extract can also be spray dried or freeze dried or lyophilized, if desired.

Following the concentration operation the resulting concentrated aqueous extract which may be at a temperature in the range 30°–95°C., such as about 40°–50°C., depending upon the pressure at which the concentration operation was carried out, is decolorized by contact with a suitable decolorizing agent, such as by passing the concentrated aqueous extract through a mass of suitable decolorizing agent, such as a bed of activated carbon or charcoal or by slurrying the concentrated aqueous extract with activated carbon or charcoal and filtering.

The resulting decolorized concentrated extract is then cooled to a temperature, such as a temperature in the range 0°–5°C., effective to precipitate or crystallize L-Dopa therefrom. The resulting L-Dopa crystals are then filtered to separate the L-Dopa-containing mother liquor which is then advantageously returned to the extraction operation or to the concentration operation to contact additional fresh L-Dopa-containing material for the extraction of L-Dopa therefrom. L-Dopa crystallization can also be effected by adding a salt, such as sodium chloride, to the concentrated L-Dopa solution to "salt out" the L-Dopa.

The separated L-Dopa crystals are desirably washed with cold water, such as ice water, e.g. water at a temperature in the range 0°–5°C., more or less, to remove an adhering mother liquor and the resulting wash liquor is also advantageously employed to extract L-Dopa from fresh L-Dopa-containing feed material, such as from fresh ground velvet bean, or returned to the L-Dopa concentration operation. Desirably, especially when it is desired to obtain a substantially pure, pharmaceutical grade L-Dopa product, the L-Dopa crystals after washing with ice water are again washed with alcohol or an alcohol-ether wash, again preferably at a reduced temperature. The resulting washed L-Dopa crystals are then dried and recovered as product.

In the extraction operation wherein the L-Dopa containing material, such as velvet bean meal, is extracted with water the water employed may be tap water, deionized water or distilled water or other suitable readily available water, such as substantially acid-free municipal water having a low dissolved solids content, such as dissolved solids content below about 500 ppm by weight.

The extraction operation wherein the ground velvet bean is extracted with water may be a continuous or a batch type operation. For example, the L-Dopa extraction operation may be carried out in a continuous countercurrent extraction operation wherein a mass of ground velvet bean is moved countercurrently with respect to a stream of water. If desired, the extraction operation may be carried out in a continuous concurrent operation wherein a stream of water and a stream of ground velvet bean are supplied to one end of an extraction zone and the extracted velvet bean and resulting L-Dopa-containing extract separately recovered from the other end of the extraction zone.

Further, if desired, the extraction operation may be carried out in a multi-stage batch extraction operation wherein in a single or plural stage contacting zone water and a mass of ground velvet bean, such as a fixed bed or a plurality of fixed beds of velvet bean, are contacted and after a sufficient length of time, from about 5 minutes to about 24 hours, e.g. 1–5 hours, depending upon the extraction temperature and the particle size of the L-Dopa-containing material being extracted, and the proportions of the water to the velvet bean being extracted. The resulting aqueous extract is separated from the extracted velvet bean and the extraction operation continued or carried out until the amount of L-Dopa in the extract or in the velvet bean residue is negligible or insufficient to warrant further extraction.

In the extraction operation it is preferred that the velvet bean be ground to a velvet bean meal having a particle size in the range from about 10 to about 20 mesh, i.e. a particle size which passes through a 10 mesh screen but is retained on a 20 mesh screen. Finer or coarser ground velvet bean or mixtures thereof are also useful, such as velvet bean meal having a particle size in the range from about 5 to about 100 mesh, more or less.

Referring now to the drawing which is a flow chart illustrative of the practices of this invention, ground velvet bean supplied via line 10 and water at a pH of about 5.0–7.0, such as acid free tap water or distilled water, supplied via line 11 in the relative proportions of about 12 liters of water per kilogram of velvet bean, estimated L-Dopa content of the bean being about 2% by weight, are brought into contact in extraction zone or tank 12 which is equipped with paddle mixer 14. Within tank 12 the ground velvet bean and water are contacted and mixed for a suitable period of time, such as from about 0.25 to about 5.0 hours, at a temperature in the range from about 15° to about 25°C.

Desirably, the extraction operation within tank 12 is carried out so that aqueous L-Dopa-containing extract therein is substantially saturated with L-Dopa. At about room temperature about 80 milligrams of L-Dopa are dissolved at saturation in 40 ml. of water.

Desirably, multiple extraction operations are carried out in tank 12. For example, a three stage or multiple extraction operation is carried out in tank 12, i.e. the same batch of ground velvet bean is extracted with, for example, a total of three volumes of water, each in the relative proportion of about 12 liters of water per kilogram of ground velvet bean. More extractions of the ground velvet bean, if desired, or required to effect the substantially complete removal of the L-Dopa content from the velvet bean may be carried out. If desired, in a three stage or three batch extraction operation the aqueous L-Dopa-containing extract from the third stage may be employed to contact and extract L-Dopa from fresh ground velvet bean or additional L-Dopa from ground velvet bean which has already been subjected to one extraction operation. Similarly, the extract from a second batch extraction operation may be employed to contact fresh ground velvet bean.

In the extraction of L-Dopa from the ground velvet bean by water it is important that the extraction operation be carried out at a temperature to minimize the extraction and/or solubilization of water-soluble constituents contained in the ground velvet bean. Desirably, therefore, the extraction operation should be carried out at a temperature of below about 25° since at temperatures above 25°C. an undesirable amount of these water-soluble difficultly filterable proteins are taken up and/or dissolved in the aqueous extract. When, however, the extraction operation is carried out at a temperature substantially below 15°C., such as a temperature below about 5°–10°C., the amount of L-Dopa dissolved in the aqueous extract is reduced, thereby necessitating a larger number of extraction operations and/or a larger amount of water and/or a longer contact time between the water and the ground velvet bean before the substantially complete removal of L-Dopa therefrom. If desired, the extraction operation can be carried out at an elevated temperature, as high as about 100°C., e.g. in the range 50°–90°C., but at such elevated extraction temperature the extraction operation is carried out in a shorter period of time, below one hour, usually within a matter of seconds to a few minutes and usually in a single extraction operation.

Following the substantially complete removal of the L-Dopa content from the ground velvet bean the resulting aqueous extract and the extracted, substantially L-Dopa-free velvet bean are passed via line 15 to centrifuge 16 wherein the extracted, substantially L-Dopa-free velvet bean is separated and removed via line 18. The resulting aqueous extract containing L-Dopa dissolved therein is recovered via line 19. Desirably, the L-Dopa-containing extract is treated with sulfur dioxide, such as by injection of gaseous sulfur dioxide via line 20 into the aqueous L-Dopa extract flowing in line 19. $SO_2$ is employed to treat the aqueous L-Dopa extract so as to avoid L-Dopa losses in the subsequent processing operation by oxidation of the extracted L-Dopa. The amount of $SO_2$ employed in the treatment of the aqueous L-Dopa-containing extract is sufficient to prevent oxidation of the extracted L-Dopa, such as an amount in the range from about 2 to 200 ppm, more or less, based on the aqueous extract flowing through line 19. If required, larger amounts of $SO_2$ may be employed to prevent darkening of the L-Dopa extract. Darkening of the extract phase is evidence of oxidation and loss of the extracted L-Dopa.

The $SO_2$-treated L-Dopa-containing extract from line 19 is passed to filter 21, such as a plate and frame filter, or other suitable filtration device for the removal of suspended solid particles from the aqueous extract. The filtration operation carried out in filter 21 is a polishing filtration operation in the sense that only a relatively small amount of solids remains to be removed from the aqueous extract. The resulting substantially solids-free filtrate leaves filter 21 via line 22 and is supplied to vacuum concentrator 24.

Within vacuum concentrator 24 the aqueous extract is concentrated, such as by the removal of a larger amount, at least 50%, of the water content, such as about 90% of the water content. The concentration operation carried out within concentrator 24 is effected at a reduced pressure, i.e. below atmospheric, such as at a pressure in the range 2 mm Hg to about 500 mm Hg absolute. Concentrator 24 is operated at a temperature not greater than about 95°C., preferably not greater than about 90°C. The water is removed from the aqueous extract undergoing concentration within concentrator 24 via line 25 and the resulting concentrated extract having an increased L-Dopa content, such as about 2.0% by weight L-Dopa, e.g. an L-Dopa concentration in the range from about 1.0–2.5% by weight and at a temperature of about 90°C. is removed from concentrator 24 via line 26 and introduced into decolorizer 27.

Within decolorizer 27 the relatively hot concentrated aqueous L-Dopa extract is brought into contact with a bed of a suitable decolorizing agent, such as activated carbon or charcoal, for the removal of color bodies from the concentrated extract. The resulting substantially color-free, substantially water-white, concentrated L-Dopa extract is removed from decolorizer 27 via line 28 and passed to cooler-crystallizer 29.

Within cooler-crystallizer 29 the temperature of the concentrated L-Dopa extract is reduced to a temperature in the range of about 0°–5°C. to effect precipitation and crystallization of L-Dopa from the concentrated extract. The resulting cooled admixture comprising L-Dopa crystals and mother liquor is then passed via line 30 to L-Dopa filter 31 for the removal of the L-Dopa crystals from the mother liquor. The L-Dopa crystals removed by filtration within L-Dopa filter 31 are washed with water, such as ice water or water at a temperature of about 0°–5°C., supplied via line 32. The liquids recovered from filter 31, including the mother liquor and the washings, are removed via line 34 and supplied via line 11 with fresh water for admixture with ground velvet bean for the extraction of L-Dopa. If desired, the recovered liquids may be passed via line 34a to vacuum concentrator 24 for concentration and eventual recovery of the L-Dopa therefrom.

The water washed L-Dopa crystals are removed from L-Dopa filter 31 and passed via line 35 and subjected to an alcohol wash (ethyl alcohol) or an alcohol-ether (ethyl ether) wash in tank 36, such as by slurrying the L-Dopa crystals in alcohol or the alcohol-ether mixture. As indicated alcohol or alcohol-ether are supplied from a suitable source via line 38 to tank 36 and the resulting alcohol or alcohol-ether wash liquid is recovered therefrom via line 39 and recycled via line 38. The resulting alcohol or alcohol-ether washed L-Dopa crystals are recovered via line 40 and after drying are packaged as product.

From time to time when a batch of the dry product L-Dopa crystals recovered via line 40 do not meet specifications the L-Dopa crystals are purified by recrystallization such as by dissolving the L-Dopa in distilled water, in the proportions of about 20 grams of L-Dopa per 750 ml. of distilled water at an elevated temperature of about 100°C. Desirably, a minor amount, e.g. about 1% by weight of the L-Dopa, of activated carbon or charcoal is included for additional decolorization or removal of trace impurities. The resulting hot admixture comprising dissolved L-Dopa and suspended activated carbon or charcoal is then filtered and the aqueous filtrate cooled to a temperature of about 0°–5°C. to crystallize L-Dopa therefrom which is then recovered by filtering and washing to yield pharmaceutical grade white L-Dopa.

The following example is illustrative of the practices of this invention:

Ground velvet bean and tap water in the proportion 1 part by weight ground velvet bean to 5 parts by weight water were mixed and the resulting admixture permitted to stand overnight at room temperature (about 20°C.). The resulting aqueous extract phase or solution was slightly brown in color. The admixture was filtered through a cake of filter aid (celite) prepared from an admixture of about 2 parts by weight celite to 1 part by weight saturated $SO_2$ solution. The extract phase filtered rapidly through the celite cake and the resulting L-Dopa solution was clear and gave a strong positive test for L-Dopa.

The filtered L-Dopa-containing extract phase or filtrate was concentrated and L-Dopa was crystallized therefrom when the concentrated filtrate was reduced in temperature.

The extracted velvet bean from the above-described extraction operation was again extracted with water in the proportion 1 part by weight bean to 5 parts by weight water and the resulting aqueous extract phase was again filtered and concentrated. The resulting concentrated extract phase gave a positive test for L-Dopa indicating that additional L-Dopa was recovered from the velvet bean in the second extraction operation. Both filtration operations were carried out without difficulty and the admixtures of velvet bean and water at room temperature filtered rapidly.

As will be apparent to those skilled in the art in the light of the foregoing disclosure, many modifications, alterations and substitutions are possible in the practice of this invention without departing from the spirit or scope thereof.

I claim:

1. A method for the recovery of L-Dopa from L-Dopa-containing material which comprises extracting L-Dopa from said material by contacting said material with substantially acid-free water, separating the resulting aqueous extract, now containing L-Dopa dissolved therein, from the resulting extracted material, concentrating the resulting aqueous extract with the removal of at least about 50% of the water content therefrom and separating L-Dopa from the resulting concentrated aqueous extract by crystallization.

2. A method in accordance with claim 1 wherein said water is tap water.

3. A method in accordance with claim 1 wherein said water is deionized water.

4. A method in accordance with claim 1 wherein said material is velvet bean and wherein the extraction of the velvet bean with water is carried out at a temperature in the range 15°–25°C.

5. A method in accordance with claim 1 wherein the extraction of said material is carried out in a continuous extraction operation.

6. A method in accordance with claim 1 wherein the extraction of said material is carried out in a fixed bed multiple batch or stage operation.

7. A method in accordance with claim 1 wherein the concentration of the aqueous extract is carried out at a maximum temperature not greater than about 90°C.

8. A method in accordance with claim 1 wherein said aqueous extract is filtered to remove any suspended solids therefrom prior to concentration.

9. A method for the recovery of L-Dopa from L-Dopa-containing material which comprises extracting L-Dopa from said material by contacting said material with substantially acid-free water, separating the resulting aqueous extract, now containing L-Dopa dissolved therein, from the resulting extracted material, adding to the resulting aqueous extract an amount of $SO_2$ sufficient to prevent oxidation of the L-Dopa in the aqueous extract, concentrating the resulting aqueous extract and separating L-Dopa therefrom by crystallization.

10. A method in accordance with claim 9 wherein the amount of $SO_2$ added to said aqueous extract is in the range 2–200 ppm based on said aqueous extract.

11. A method in accordance with claim 9 wherein the resulting concentrated extract is decolorized prior to separating L-Dopa by crystallization.

12. A method in accordance with claim 9 wherein the resulting concentrated extract is decolorized by contact with an activated carbon prior to separating L-Dopa by crystallization.

13. A method in accordance with claim 9 wherein the resulting concentrated extract is decolorized by contact with activated carbon and filtered to remove any suspended solids therefrom prior to separating L-Dopa by crystallization.

14. A method in accordance with claim 9 wherein the crystallized L-Dopa is recovered and washed with water at a temperature of about 0°–5°C.

15. A method in accordance with claim 9 wherein the resulting crystallized L-Dopa is recovered and washed with water and the resulting wash water recovered and employed in the extraction operation wherein said material is extracted with water.

16. A method in accordance with claim 9 wherein the resulting crystallized L-Dopa is recovered and washed with water at a temperature of about 0°–5°C. and washed again with ethyl alcohol.

17. A method in accordance with claim 9 wherein the resulting crystallized L-Dopa is washed with water at a temperature of about 0°–5°C. and washed again with ethyl alcohol and ethyl ether.

18. A method for the recovery of L-Dopa from ground velvet bean which comprises grinding velvet bean to a mesh size of approximately 10–20 mesh, contacting the ground velvet bean with distilled water at a temperature in the range from about 15° to about 25°C. to extract L-Dopa therefrom, the amount of water employed to extract the L-Dopa from the ground velvet bean being about 36 liters of water per kilogram of ground velvet bean, separating the extracted ground velvet bean from the aqueous extract containing L-Dopa dissolved therein, treating the resulting aqueous extract with gaseous $SO_2$ in an amount effective to prevent oxidation of the L-Dopa therein, filtering the resulting aqueous extract to remove suspended solids, concentrating the resulting treated aqueous extract by subjecting the extract to evaporation at a reduced pressure to remove about 90% of the water therefrom, the concentration operation being carried out at a temperature in the range about 30°–95°C., subjecting the resulting concentrate to decolorization by contact with activated carbon at a temperature in the range 85°–95°C., filtering the resulting decolorized concentrate to remove suspended solids therefrom, cooling with agitation the resulting filtered concentrate to a temperature in the range from about 0° to about 5°C. to crystallize L-Dopa, separating the resulting crystallized L-Dopa by filtration, washing the resulting separated L-Dopa crystals with water at a temperature of about 0°C. followed by a second washing operation with a washing liquid selected from the group consisting of ethyl alcohol and a mixture of ethyl alcohol and ethyl ether.

19. A method for recovering 3-(3,4-dihydroxyphenyl)-L-alanine from comminuted beans containing it, which comprises the steps of contacting said beans with a reagent consisting essentially of liquid water at a temperature in the range about 5°–100°C. for a period of time to dissolve a substantial portion of the 3-(3,4-dihydroxyphenyl)-L-alanine therein, separating the extract phase from the beans and recovering a 3-(3,4-dihydroxyphenyl)-L-alanine product.

* * * * *